US012632598B2

(12) United States Patent
Huang et al.

(10) Patent No.: US 12,632,598 B2
(45) Date of Patent: May 19, 2026

(54) SYSTEM AND METHOD FOR REVERSIBLY DEIDENTIFYING MEDICAL IMAGERY

(71) Applicant: Gradient Health, Inc., Durham, NC (US)

(72) Inventors: Ouwen Huang, Durham, NC (US); Chang Liu, Durham, NC (US); Joshua Miller, Durham, NC (US)

(73) Assignee: Gradient Health, Inc., Durham, NC (US)

(*) Notice: Subject to any disclaimer, the term of this patent is extended or adjusted under 35 U.S.C. 154(b) by 9 days.

(21) Appl. No.: 18/680,390

(22) Filed: May 31, 2024

(65) Prior Publication Data

US 2024/0411927 A1 Dec. 12, 2024

Related U.S. Application Data

(60) Provisional application No. 63/471,385, filed on Jun. 6, 2023.

(51) Int. Cl.
| | |
|---|---|
| *G06F 21/62* | (2013.01) |
| *G06V 30/14* | (2022.01) |
| *G06V 30/148* | (2022.01) |
| *G06V 30/19* | (2022.01) |
| *G16H 30/20* | (2018.01) |

(52) U.S. Cl.
CPC ...... *G06F 21/6254* (2013.01); *G06V 30/1448* (2022.01); *G06V 30/15* (2022.01); *G06V*

*30/19* (2022.01); *G16H 30/20* (2018.01); *G06V 2201/03* (2022.01)

(58) Field of Classification Search
CPC .... G06F 21/6254; G16H 30/20; G06V 30/19; G06V 30/15; G06V 30/1448
See application file for complete search history.

(56) References Cited

U.S. PATENT DOCUMENTS

| | | | |
|---|---|---|---|
| 7,519,591 B2 | 4/2009 | Landi et al. | |
| 8,898,798 B2 | 11/2014 | Rogers et al. | |
| 10,722,210 B2 | 7/2020 | Yu | |
| 10,817,622 B2 | 10/2020 | Rosenberg et al. | |
| 10,869,608 B2 | 12/2020 | Dormer et al. | |
| 11,183,292 B2 | 11/2021 | Stalling et al. | |
| 2016/0335397 A1* | 11/2016 | Blum | G16H 10/60 |
| 2021/0264054 A1 | 8/2021 | Anson et al. | |
| 2022/0075903 A1 | 3/2022 | Prasad et al. | |
| 2022/0215948 A1* | 7/2022 | Bardot | G16H 40/40 |
| 2023/0065967 A1* | 3/2023 | Sughrue | G16H 30/20 |

* cited by examiner

*Primary Examiner* — Clayton R Williams
(74) *Attorney, Agent, or Firm* — NK Patent Law

(57) ABSTRACT

A system for reversibly deidentifying images uses optical character recognition (OCR) or another method of automatically determining pixels to edit or remove within a medical image. One or more keys are generated encoding the original pixel values and pixel locations for the edited or removed pixels, and are stored on at least one server or at a medical institution that originally created the images. The encrypted data is stored in a DICOM header of the image files. Upon request, keys are able to be provided to restore at least some of the original pixels of the medical images.

20 Claims, 5 Drawing Sheets

SYSTEM AND METHOD FOR REVERSIBLY DEIDENTIFYING MEDICAL IMAGERY

CROSS-REFERENCE TO RELATED APPLICATIONS

This application is related to and claims priority from the following US patents and patent applications: this application claims priority from and the benefit of U.S. Provisional Patent Application No. 63/471,385, filed Jun. 6, 2023, which is incorporated herein by reference in its entirety.

BACKGROUND OF THE INVENTION

1. Field of the Invention

The present invention relates to deidentification of medical images, and more specifically to reversible deidentification of medical images using cryptographic hashes.

2. Description of the Prior Art

It is generally known in the prior art to provide methods for deidentifying medical images by means of optical character recognition (OCR) for identifying and blacking text within the images.

Prior art patent documents include the following:

U.S. Pat. No. 10,817,622 for Systems and methods for de-identifying medical and healthcare data by inventors Rosenberg et al., filed Nov. 5, 2019 and issued Oct. 27, 2020, discloses systems and methods for protecting patient privacy when health care information is shared between various entities and, in particular, to systems and methods that implement a multi-stage sanitizing routine for de-identifying patient data from medical reports and diagnostic images to ensure patient privacy, while preserving the ability for sanitized medical reports and diagnostic images to be re-identified.

US Patent Pub. No. 2022/0075903 for Method for Securely Storing and Retrieving Medical Data by inventors Prasad et al., filed Sep. 9, 2021 and published Mar. 10, 2022, discloses a gateway and a method for securely storing (and/or securely retrieving) medical data the method for storing comprising at least steps of: obtaining, in a secure environment, medical data which include patient property data as well as patient identifier data wherein the patient identifier data indicate at least one patient to which the patient property data correspond; generating, in the secure environment de identified medical data by replacing the patient identifier data in the medical data with non-patient-identifying coded identifiers; generating, in the secure environment, a re-identifying database indicating correspondences between the non-patient-identifying coded identifiers and the patient identifier data; generating n encrypted re-identifying database by applying, in the secure environment, at least one symmetric and/or asymmetric encryption method to the re-identifying database; storing the encrypted re-identifying database and the de-identified medical data on a cloud storage outside of the secure environment.

U.S. Pat. No. 10,869,608 for Medical imaging and efficient sharing of medical imaging information by inventors Dormer et al., filed Nov. 29, 2016 and issued Dec. 22, 2020, discloses an MRI image processing and analysis system identifying instances of structure in MRI flow data, e.g., coherency, derive contours and/or clinical markers based on the identified structures. The system may be remotely located from one or more MRI acquisition systems, and perform: error detection and/or correction on MRI data sets (e.g., phase error correction, phase aliasing, signal unwrapping, and/or on other artifacts); segmentation; visualization of flow (e.g., velocity, arterial versus venous flow, shunts) superimposed on anatomical structure, quantification; verification; and/or generation of patient specific 4-D flow protocols. A protected health information (PHI) service is provided which de-identifies medical study data and allows medical providers to control PHI data, and uploads the de-identified data to an analytics service provider (ASP) system. A web application is provided which merges the PHI data with the de-identified data while keeping control of the PHI data with the medical provider.

US Patent Pub. No. 2021/0264054 for Re-Identifying Pseudonymized or De-Identified Data Utilizing Distributed Ledger Technology by inventors Anson et al., filed Feb. 24, 2020 and published Aug. 26, 2021, discloses a system, method, and computer-readable medium for providing auditability of a distributed ledger technology (DLT) of de-identified data of entities, stored in the DLT. In certain embodiments, data related to an entity is de-identified. The de-identified data is stored in the DLT. Access to the de-identified data is determined. Instances of access to the de-identified data is recorded to the DLT. In certain embodiments, information used to re-identify the de-identified data is store on the DLT. Access to the information can also be determined and recorded to the DLT.

U.S. Pat. No. 8,898,798 for Systems and methods for medical information analysis with deidentification and reidentification by inventors Rogers et al., filed Oct. 19, 2012 and issued Nov. 25, 2014, discloses a medical information navigation engine useful in association with at least one electronic health record system. The engine decouples identifying information from clinical data from electronic health records. The clinical data includes clinical narrative having discrete data and textual data. The identifying information is stored. Additionally, the identifying information is associated with a token in the clinical data. The clinical data may then be indexed. The discrete data and the textual data in the clinical data may then be mined. Mining includes extracting at least one relevant event from the discrete data and the textual data. Next, the clinical data and identifying information may be reintegrated using the token. The event associated with the mined discrete data and textual data may then be exported. The system may also provide a validation tool for users, including clinicians, to search and view clinical data. The exported event may be used to alter treatment of a patient.

U.S. Pat. No. 7,519,591 for Systems and methods for encryption-based de-identification of protected health information by inventors Landi et al., filed Mar. 9, 2004 and issued Apr. 14, 2009, discloses systems and methods for protecting individual privacy (e.g., patient privacy) when individual data records (e.g., patient data records) are shared between various entities (e.g., healthcare entities). In one aspect, systems and methods are provided which implement secured key encryption for de-identifying patient data to ensure patient privacy, while allowing only the owners of the patient data and/or legally empowered entities to re-identify subject patients associated with de-identified patient data records, when needed.

U.S. Pat. No. 11,183,292 for Method and system for rule-based anonymized display and data export by inventors Stalling et al., filed Jul. 26, 2016 and issued Nov. 23, 2021, discloses a system for implementing a rule derived basis to display anonymized image sets. In various embodiments of the invention, users with the appropriate permission can launch a function inside a system in order to anonymize and export the currently loaded study or studies, or one or more studies identified by a search criteria. The data from the studies that were identified is then anonymized on the system using predefined rules. In an embodiment of the present invention, the data from selected studies is anonymized on a server, and only then transmitted to another network device thus minimizing the risk that protected health information can be inadvertently disclosed. In an alternative embodiment of the present invention, the data from selected studies is anonymized on a server, and only the anonymized data is stored to the hard disk or other media of a user viewing the study.

U.S. Pat. No. 10,722,210 for Method for memorable image generation for anonymized three-dimensional medical image workflows by inventor Yu, filed Dec. 14, 2017 and issued Jul. 28, 2020, discloses systems and methods for generating a two-dimensional image for identification of medical imaging data. An image processor acquires the medical imaging data and determines a category of the medical imaging data. A machine-learnt network identifies as a function of the category, a plurality of settings of rendering parameters that highlight one or more features the medical imaging data. The image processor renders the two-dimensional identifier image from the medical imaging data using the plurality of settings of rendering parameters and stores the medical imaging data with the two-dimensional identifier image.

SUMMARY OF THE INVENTION

The present invention relates to deidentification of medical images, and more specifically to reversible deidentification of medical images using cryptographic hashes.

It is an object of this invention to provide a method that allows for reversible deidentification such that unintentionally removed material from an image is able to be re-added.

In one embodiment, the present invention includes a system for reversibly deidentifying medical images, including a server configured to receive medical images including one or more protected health information (PHI) regions, an artificial intelligence module configured to identify the one or more PHI regions in the medical images and define one or more bounding boxes around the identified one or more PHI regions, wherein the artificial intelligence module automatically clips the one or more bounding boxes out of the medical images and generates one or more encrypted image files of the one or more bounding boxes, wherein at least one cryptographic hash is generated for the one or more bounding boxes based on locations and pixel values for pixels within the one or more bounding boxes, and wherein the at least one cryptographic hash is operable to be used to readd the one or more encrypted image files into the medical images.

In another embodiment, the present invention includes a method for reversibly deidentifying medical images, including receiving medical images including one or more protected health information (PHI) regions, an artificial intelligence module identifying the one or more PHI regions in the medical images and defining one or more bounding boxes around the identified one or more PHI regions, the artificial intelligence module automatically clipping the one or more bounding boxes out of the medical images and generating one or more encrypted image files of the one or more bounding boxes, and generating at least one cryptographic hash for the one or more bounding boxes based on locations and pixel values for pixels within the one or more bounding boxes, wherein the at least one cryptographic hash is operable to be used to readd the one or more encrypted image files into the medical images.

In yet another embodiment, the present invention includes a system for deanonymization of medical images, including a server configured to transmit medical image files to a recipient device, wherein the medical image files include a primary anonymized medical image, wherein the primary anonymized medical image includes one or more bounding boxes corresponding to removed protected health information (PHI), and one or more encrypted subimages of cropped portions of the primary anonymized medical images corresponding to the one or more bounding boxes, wherein the server receives a request from the recipient device designating at least one of the one or more bounding boxes to be removed or altered, wherein the server transmits at least one cryptographic key to the recipient device in response to the request, and wherein the at least one cryptographic key enables at least one of the one or more encrypted subimages to be reintegrated into the primary anonymized medical image.

These and other aspects of the present invention will become apparent to those skilled in the art after a reading of the following description of the preferred embodiment when considered with the drawings, as they support the claimed invention.

DETAILED DESCRIPTION

Figure 1A:
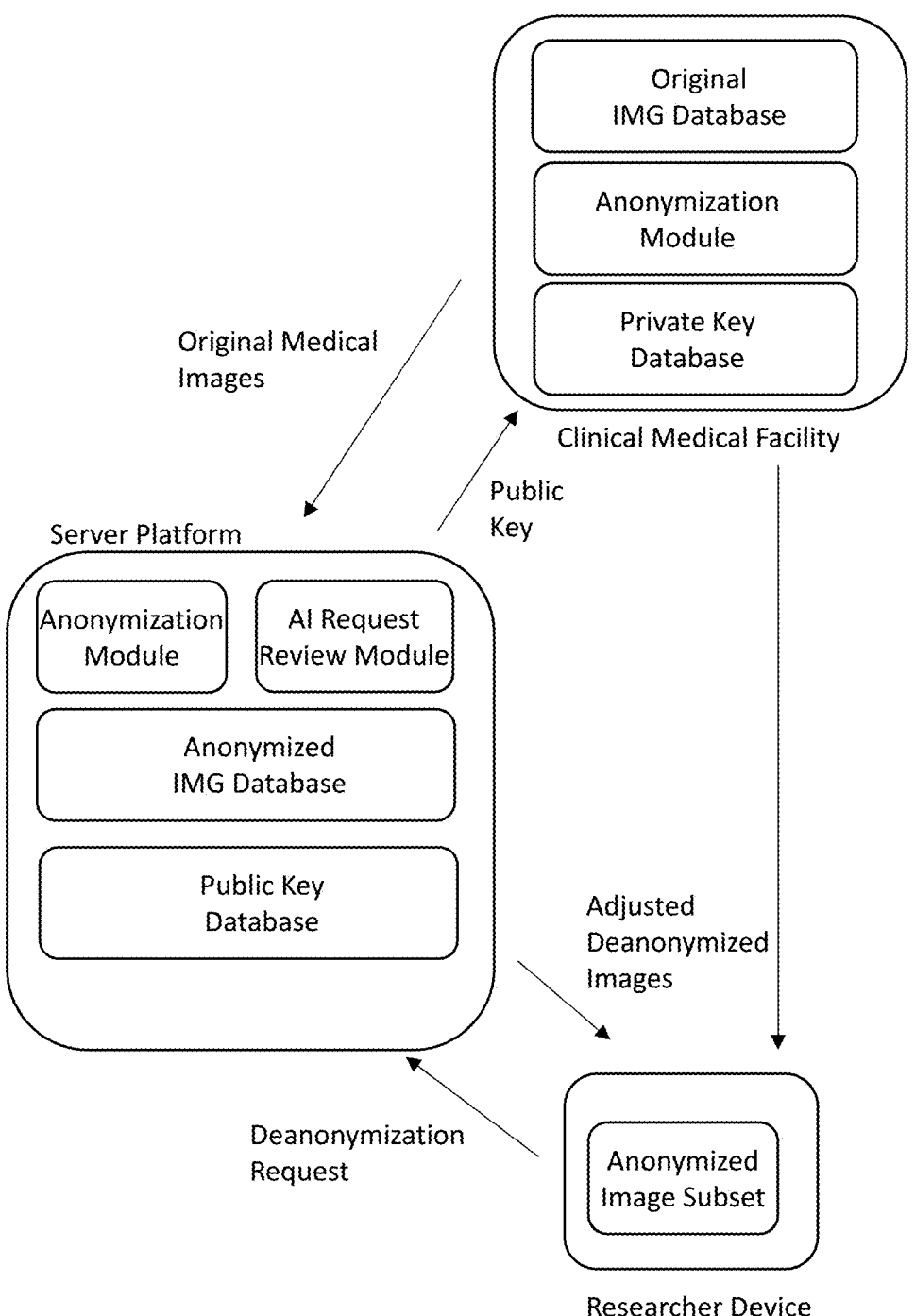
FIG. 1A illustrates a schematic diagram for a system of anonymizing and deanonymizing medical images according to one embodiment of the present invention.

The present invention is generally directed to deidentification of medical images, and more specifically to reversible deidentification of medical images using cryptographic hashes.

In one embodiment, the present invention includes a system for reversibly deidentifying medical images, including a server configured to receive medical images including one or more protected health information (PHI) regions, an artificial intelligence module configured to identify the one or more PHI regions in the medical images and define one or more bounding boxes around the identified one or more PHI regions, wherein the artificial intelligence module automatically clips the one or more bounding boxes out of the medical images and generates one or more encrypted image files of the one or more bounding boxes, wherein at least one cryptographic hash is generated for the one or more bounding boxes based on locations and pixel values for pixels within the one or more bounding boxes, and wherein the at least one cryptographic hash is operable to be used to readd the one or more encrypted image files into the medical images.

In another embodiment, the present invention includes a method for reversibly deidentifying medical images, including receiving medical images including one or more protected health information (PHI) regions, an artificial intelligence module identifying the one or more PHI regions in the medical images and defining one or more bounding boxes around the identified one or more PHI regions, the artificial intelligence module automatically clipping the one or more bounding boxes out of the medical images and generating one or more encrypted image files of the one or more bounding boxes, and generating at least one cryptographic hash for the one or more bounding boxes based on locations and pixel values for pixels within the one or more bounding boxes, wherein the at least one cryptographic hash is operable to be used to readd the one or more encrypted image files into the medical images.

In yet another embodiment, the present invention includes a system for deanonymization of medical images, including a server configured to transmit medical image files to a recipient device, wherein the medical image files include a primary anonymized medical image, wherein the primary anonymized medical image includes one or more bounding boxes corresponding to removed protected health information (PHI), and one or more encrypted subimages of cropped portions of the primary anonymized medical images corresponding to the one or more bounding boxes, wherein the server receives a request from the recipient device designating at least one of the one or more bounding boxes to be removed or altered, wherein the server transmits at least one cryptographic key to the recipient device in response to the request, and wherein the at least one cryptographic key enables at least one of the one or more encrypted subimages to be reintegrated into the primary anonymized medical image.

When medical images (e.g., X-rays, computed tomography (CT) scans, etc.) are taken, identifying information is often inserted into or otherwise added to the image denoting information such as the name, age, sex, identification number, image resolution, which side of the patient the image was taken from, and other information that provides context to the image. This information is often important for a radiologist to have such that the radiologist is able to be certain that they are looking at the information from the correct patient. Furthermore, it is important that the correct part of the patient's body be identified (e.g., right knee vs. left knee).

However, while this information is beneficial for clinical practice, it often needs to be removed when used for research purposes. In order to develop, for example, models to use machine learning to identify particular medical issues that are identifiable from particular types of medical imagery, the machine learning model needs to have existing medical imagery data in order to train the model. Many universities and other research institutions require that patient data be deidentified before the images are able to be analyzed and used to generate research data, primarily for patient privacy purposes. Identifying patient information includes the broad categories of Protected Health Information (PHI), which is specifically protected, and Personally Identifiable Information (PII), which is less strictly protected. Broadly, according to the Health Insurance Portability and Accountability Act (HIPAA), deidentification of patient data is able to happen by one of two processes. The first process removes all data within 18 categories of personal identifiers, while the other leaves some of the identifiers (commonly date and demographic data), while removing other deidentifiers and relying on expert assurance that the remaining identifiers are not capable of being used for reidentification purposes. For the purposes of medical images, deidentification means that the aforementioned text fields need to be removed or covered up.

At a metadata data and data sourcing level, the Digital Imaging and Communications in Medicine (DICOM) format is primarily used as a means to transmit and anonymize patient data, as DICOM files are stripped of metadata through a cloud application programming interface (API) such that the originating hospital, geographic location, date, time, and other identifying information is unable to be determined based on the file. However, existing Cloud API systems used for DICOM files do not act within the image to strip identifying information embedded within the image itself. In the past, much of medical deidentification was performed manually, creating a laborious and time consuming process subject to human error. However, manual deidentification is increasingly impractical as more and more medical data is generated and a higher percentage of that data is desired by researchers seeking to automate other areas of medicine. The most common method of automatic deidentification of images is to use optical character recognition (OCR) to identify text and then place a black box over the text such that it is no longer able to be read, as described in documents such as U.S. Patent Publication No. 2018/0068068, which is incorporated herein by reference in its entirety. While numerous different services offer such image deidentification, the methods used are highly consistent in 1. Recognizing text, and 2. Blurring or blacking it out.

Automatic deidentification systems do not have 100% accuracy, and, if systematically faulty for a given type of image, have the potential to destroy large amounts of useful medical imagery data through overzealous deidentification. For example, for an X-ray of a lung, if the process accidentally blacks out space in the middle of the chest, that fault is easily able to be ruin the ability to use the image for analysis purposes, as it possibly covers diagnostic features in the image and isn't useful for training as a large artifact is then present in the middle of the training data.

Some methods of supposed reidentification have been proposed in prior art literature, in part to note concerns that such reidentification methods are able to be used to gather patient identifying information by holders of the deidentified images, raising privacy concerns. One such article is "Deep learning-based patient re-identification is able to exploit the biometric nature of medical chest X-ray data" by Packhauser et al., which was published in 2022. The prior art proposes that deep learning models are able to determine, with a high degree of accuracy, whether two images of the same body part (in this case a chest) belong to the same patient. However, these deep learning methods differ from the present invention in at least two important respects. First, by associating two images with prior art deep learning models, the researchers are able to aggregate data that could potentially be used to identify the patient. Second, the prior art technique doesn't resolve the issue of missing data within any one image, and is only focused on associating two images. What is needed is a system that allows for reversible deidentification, especially lossless reversible deidentification, of image data, allowing for readdition of unintentionally removed artifacts of the deidentification process without producing new connections that apply additional personal identifiers to the analyzed images.

It should be noted that while some other papers discuss reidentification of medical image data, most notably "Reversible Anonymization of DICOM Images using Cryptography and Digital Watermarking" by Zaz et al., other references refer to the ability for a single system to cryptographically insert and subsequently remove watermarks from the image, including those watermarks that provide patient data. Thus, Zaz et al. deals chiefly with the ability to add watermarked identifying data in a way that later allows for removal, controlling both the addition and the subtraction process. Zaz et al. therefore describes a sort of closed-loop system. This is distinct, however, from a system that must deal with data that was already burned into the image by a third-party system and must subsequently be removed while still allowing for restoration of the image. Realistically, when anonymizing data, it is more convenient to act on images that don't have such burned in data, like Zaz et al. has the convenience to do, but much of the time this is not possible as it is standard procedure for many hospitals as the method they use to add identifying data to an image does not allow for digital removal in way that doesn't risk removing portions of the image itself.

Referring now to the drawings in general, the illustrations are for the purpose of describing one or more preferred embodiments of the invention and are not intended to limit the invention thereto.

The system of the present invention includes a server platform in network communication with a plurality of distributed devices, which is operable to receive data from and transmit data to the plurality of distributed devices. In one embodiment, the plurality of distributed devices include computers, smart phones, smart watches, internet-of-things (IoT) enabled devices, and/or other devices. The plurality of distributed devices receive image data from an image producing device (e.g., an X-ray scanner, a CT machine, etc.) or from another of the plurality of distributed devices (e.g., from another computer or smart phone). The images received by the plurality of distributed devices include identifying text information corresponding to a patient including, but not limited to, a name, an age, a date of birth, a unique patient identification number, a date the image was taken, a time the image was taken, a gender, a sex, an ethnicity, a race, a part of the body being imaged, and/or other personal information. One of ordinary skill in the art will understand that not all images will have the same identifying information, not all information will be presented the same way across all types of images, and not all information will be located at the same place on each image.

Figure 2:
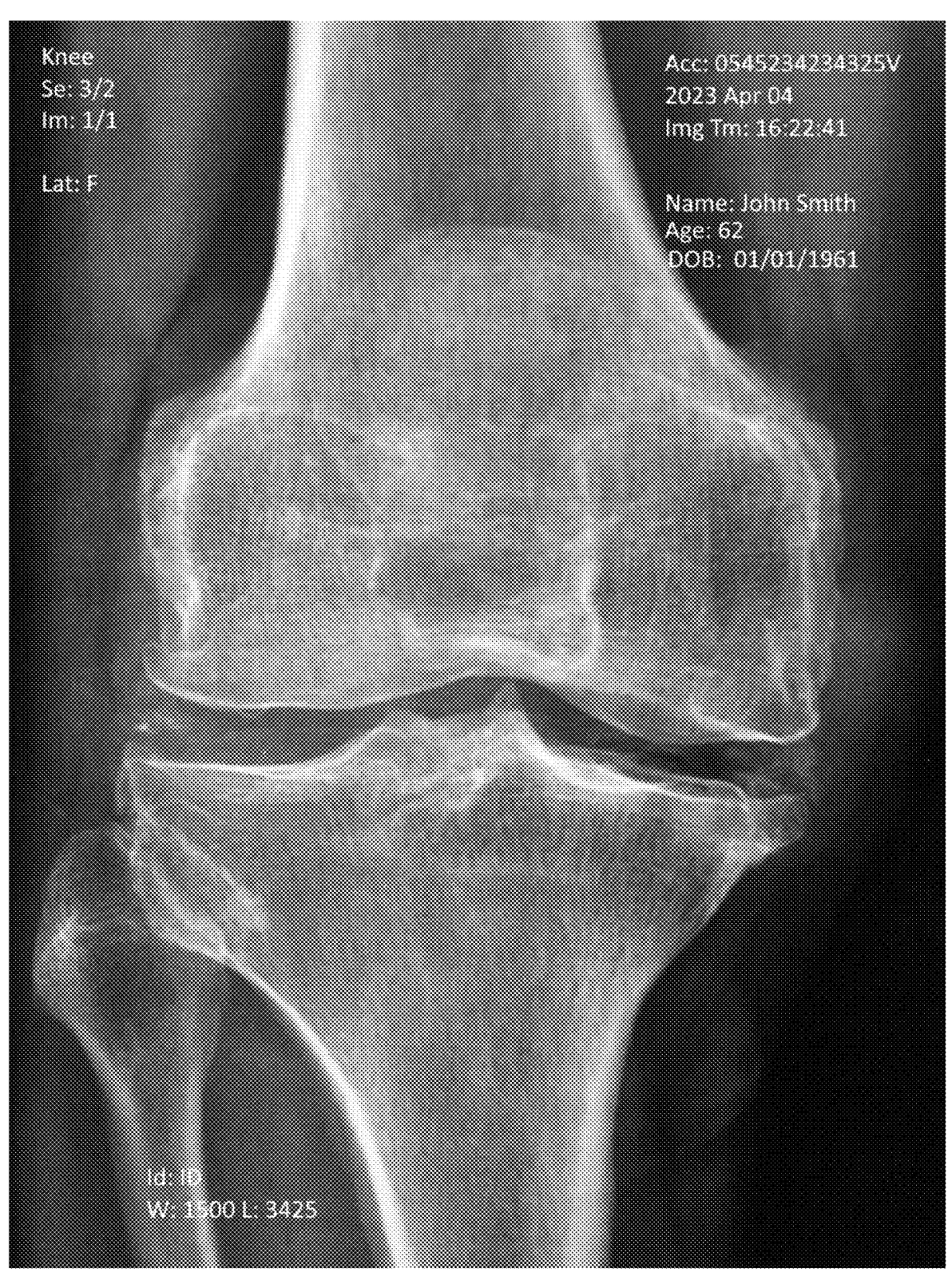
FIG. 2 illustrates an identifying X-ray image of a knee according to one embodiment of the present invention.
Figure 3:
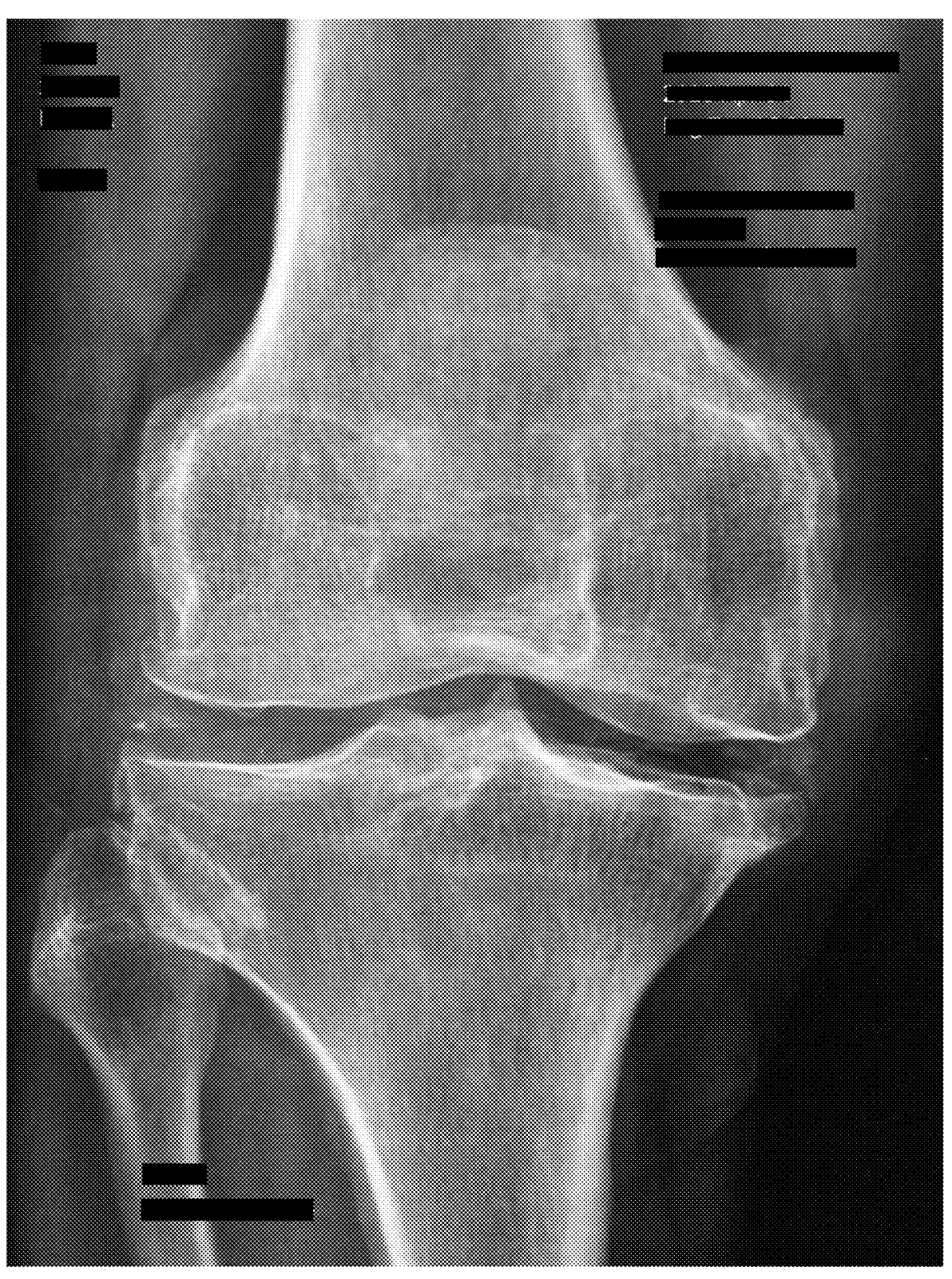
FIG. 3 illustrates a deidentified X-ray image of a knee according to one embodiment of the present invention.

At least one OCR program or other protected health information (PHI) deidentification software analyzes one or more of the images and automatically removes and/or blacks out (i.e., places a black box over) the identifying text information such that the information is no longer visible or legible. Examples of systems able to be used to deidentify the information include any known in the prior art, including those described in as U.S. Patent Publication No. 2018/0068068 and U.S. Patent Publication No. 2016/0307063, which are incorporated herein by reference in its entirety. FIG. 2 provides an example image of an X-ray before deidentification and FIG. 3 provides an example image of an X-ray after deidentification according to one embodiment of the present invention.

In one embodiment, a local copy of the original medical images with the identifying information are stored on a remote cloud server and/or a local server of the medical institution that generated the images. In one embodiment, the local copy of the original medical images are tagged with a unique identifying code corresponding to at least one unique identifying code tagged on the deidentified medical images, such that the original and deidentified versions of the images are able to be associated. In another embodiment, an original copy of the complete medical images is not saved, with only the deidentified image and individual images of the removed portions being saved anywhere. In one embodiment, the deidentified version of the medical images are uploaded to at least one cloud computing system.

In one embodiment, the deidentified version of the medical images are uploaded to the at least one cloud computing system according to the DICOM standard. In one embodiment, the medical images are stripped of metadata including, but not limited to, a time of creation, a date of creation, a point of origin, and/or other identifying information. However, in one embodiment, the medical images retain at least one unique code that allows them to be matched with an original image, but which contains no other identifying information.

In a preferred embodiment, a detection algorithm is first run on an image file to identify bounding boxes for areas with protected health information in the image. The locations of the bounding boxes are marked and stored in at least one metadata file. In one embodiment, the at least one metadata file includes at least one Javascript Object Notation (JSON) file. The bounding box areas of the image file are clipped out of the image, generating a deidentifying image file, and each of the bounding box areas are saved separately as separate image files. The separate image files are then encrypted with a key and all unencrypted versions of the bounding box images are then deleted. A total file is then saved with the deidentified image file, the at least one metadata file, and the bounding box image files are stored within. In one embodiment, the total file is a DICOM file. In one embodiment, the encrypted pixels are stenographically etched into the removed region of interest. In this embodiment, the encrypted information is directed included in the file, but appears just as noise or is not noticeable at all to a viewer of the image.

In this system, a single master key is able to be used to decrypt all of the encrypted bounding box image files. However, a plurality of subkeys are able to be generated for each bounding box image file individually which are able to decrypt only one image file each. In one embodiment, the plurality of subkeys are generated by hashing the master key with an ID for each bounding box image. In one embodiment, the single master key and the plurality of subkeys are not sent with the rest of the file and are held by either the original medical institution, or a third party management server.

In one embodiment, each file as a universally unique identifier (UUID) (e.g., StudyUID for DICOM files) and each bounding box also has a UUID (e.g., a uuidv4). The obtain a subkey for a single bounding box, the following process is performed: hash (hash (M, studyUID), bboxUID), where M is the master key for the whole file and bboxUID is the UUID for the single bounding box. The sub key produced by this process is then able to be used to decrypt just that single bounding box and nothing else, which is useful for providing more granular permissions. Therefore, if permission is granted to decrypt the entire file, then hash (M,studyUID) is provided, which is then able to be used to generate all the keys of interest as follows, where N is the number of bounding boxes:

$$\text{hash(hash}(M, studyUID), bboxUID\_1)$$

$$\text{hash(hash}(M, studyUID), bboxUID\_2)$$

$$\vdots$$

$$\text{hash(hash}(M, studyUID), bboxUID\_N)$$

This process of creating sub keys is also able to be applied to json fields, as well, with the process hash (hash (M, studyUID), 'field_name+salt'). An example of this process for a patient name in particular is hash (hash (M, studyUID), 'PatientName'+'Fn$fjslw'), with the salt being an optional protection against rainbow table attacks.

In another embodiment, for all pixels edited or removed as a result of the deidentification process, the pixel value (e.g., hex color value, etc.) and the pixel location (i.e., x-y coordinate within the image) are noted. A public key is generated for the edited or removed pixels, wherein the public key encodes the pixel values and/or pixel locations. In one embodiment, the public key is hashed to generate a shorter string. In one embodiment, the original public key or a hashed version of the public key is included in the header of the image file uploaded according to the DICOM standard. In one embodiment, a corresponding private key is then generated for the image file. However, unlike the public key, the private key is not inserted into header of the DICOM file, but instead stored in a cloud server or at the medical institution where the images are generated and associated with the unique code associated with the image file.

In one embodiment, a plurality of public keys and private keys (symmetric keys or asymmetric keys) are generated for one or more images. In one embodiment, separate public keys and private keys are generated for the pixel values versus the pixel locations. In another embodiment, the system detects each set of edited or removed pixels within the image, where a set of edited or removed pixels is defined as a group of edited or removed pixels that do not include any pixels adjacent to any pixels in any other set of edited or removed pixels. In one embodiment, separate public keys and private keys are generated for each different set of edited or removed pixels, which are saved as their own image files (e.g., JPEG files). By producing separate public keys and private keys for different sets of pixels, those pixels are able to be selectively added back into the image, rather than entirely re-adding or reedited all originally modified pixels. In one embodiment, each medical image has its own master key, application of which allows for total restoration of the original image, and a plurality of subkeys, which each allow for restoration of only a portion of the original image.

In the DICOM standard, the header includes the first few packets of information transmitted with the image file, which commonly stores demographic information about the patient and/or information regarding the image, including acquisition parameters for the imaging, image dimensions, color space, and/or other information. The header is followed by the part of the image file that actually encodes the pixel intensity data through a series a sequence of binary digits. Editing this header is what allows patient information to be removed when the image is uploaded to the cloud API associated with the DICOM standard. The header then also serves as a useful tool in associating the public key denoting the removed sections with the image or images.

When a research institution needs to re-add specific pixels within the image, which were improperly or overzealously removed during deidentification, a network device at the research institution transmits a request to at least one server (e.g., a cloud server) accompanied with the unique code associated with the image. In one embodiment, the request also includes a designated section of the image that needs to be retrieved. In one embodiment, if the private key is stored on the server level, the at least one server then transmits the private key to the transmitting device at the research institution, allowing for reversal of the deidentification process. In another embodiment, if the private key is stored at the original medical institution, the server level transmits a request for the private key to the medical institution. The medical institution is then able to grant or reject the request and optionally transmit (via at least one device at the medical institution) the private key to the at least one server, which is then able to transmit the private key to the device at the research institution. In one embodiment, the medical institution directly receives the request and is able to confirm or deny the request, or partially confirm the request, based on examination of whether the requested restoration of the image will actually reveal patient information.

In one embodiment, requests whether to transmit the private key to the research institution are based on the requested section to be added. In one embodiment, the requested section is manually reviewed for potentially identifying information and the request is denied if it includes such identifying information. In another embodiment, the requested section is automatically reviewed by at least one artificial intelligence module for determining if the requested section includes text and/or if the text in the removed section includes identifying information or other, non-identifying information (e.g., what side of the body the image was taken on). In one embodiment, the at least one artificial intelligence module used to review the requested section uses a distinct model relative to the system used for the original deidentification, in order to prevent the system from perpetuating its own decision-making. By providing a review process, whether manual or automatic, the system is able to ensure that the research institution is able to optimally obtain necessary research data, while ensuring the necessary privacy of the patient. In one embodiment, where there are multiple private keys encoding different groups of edited or removed pixels, the system is able to provide only those private keys corresponding to sections of the image that were improperly removed and do not include identifying information. Importantly, this system never requires that the actual, original image itself is ever transferred away from a secure server or from the original medical institution, decreasing the risk of compromising sensitive patient information.

In one embodiment, shown in FIG. 1A, the server platform acts as a mediator between researchers utilizing anonymized PHI data and the original producing medical facility. This provides for a greater degree of confidentiality in obfuscating the relationship between producer and user of the data and reduces the likelihood of the researcher applying pressure on the medical facility directly. In this embodiment, either the medical facility transmits the original medical image to the server platform and the server platform anonymizes the image, or the medical facility anonymizes the image before transmitting the image to the server platform. The server platform preferably does not save an original version of the image, for privacy, though one of ordinary skill in the art will understand that such an embodiment is contemplated from a technical perspective. In one embodiment, the server platform includes a database of anonymized versions of the medical images, allowing the server platform to grant access to anonymized data without requiring requests to be pinged to the medical facility each time any data is requested. In one embodiment, the server platform includes a database storing one or more public keys for each of the anonymized medical images. Preferably, the clinical medical facility includes a database of the original medical images and/or a database of private keys able to deanonymize portions of the medical images without requiring comparison to a stored copy of the original images.

In this embodiment, the server platform is able to receive deanonymization requests from the researcher device for one or more specific portions of the image. Either the server platform includes its own artificial intelligence (AI) request review module to determine if the requested areas include sensitive data, or the clinical medical facility performs that function in-house after the request is passed to it by the server platform. In one embodiment, server platform communicates the request, including, one or more public keys for the image to be accessed, to the medical facility. Preferably, the server platform then receives back a partially deanonymized version of the image back and passes this along to the researcher device, but one of ordinary skill in the art will understand that, in another embodiment, the clinical medical facility directly communicates the partially deanonymized version to the researcher device. In one embodiment, the server platform automatically updates the anonymized image database with the partially deanonymized image, allowing the system to ensure less requests from other research institutions need be made in the future.

Figure 1B:
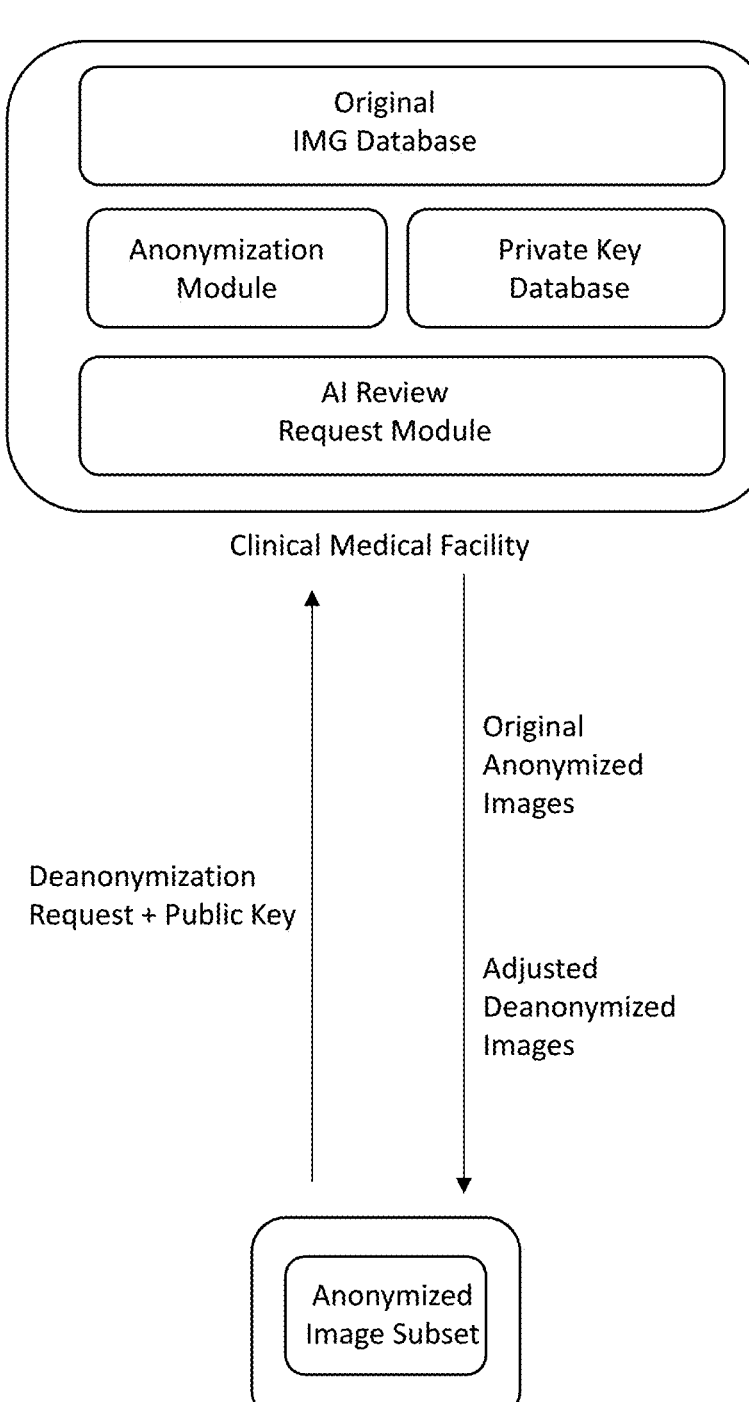
FIG. 1B illustrates a schematic diagram for a system of anonymizing and deanonymizing medical images according to one embodiment of the present invention.

In another embodiment, shown in FIG. 1B, communication occurs directly between the medical facility and the researcher device. In this embodiment, the clinical medical facility is able to perform anonymization of the image and store anonymized and/or original versions of the images, as well as private keys for deanonymizing the images. In this embodiment, the clinical medical facility receives deanonymization requests directly and sends partially deanonymized versions of the image directly back to the requesting device. In this embodiment, the clinical medical facility includes the artificial intelligence module for reviewing the requests to ensure compliance with patient anonymity.

In one embodiment, both the deidentification and reidentification processes according to the present invention are lossless, allowing for complete restoration of the image in the original quality. However, one of ordinary skill in the art will understand that the present invention is also compatible with lossy systems as well.

While one of ordinary skill in the art will understand that prior art methods of image PHI anonymization are compatible with the present invention, in a preferred embodiment, the present invention employs a new method of anonymization that performs the anonymization step on a compressed version of the image. One issue of PHI anonymization being performed outside of the hospital or other medical facility that generates the patient data is the increased potential for leaks of pre-anonymized image due to multiple parties handling the content and due to any potential vulnerabilities in the step of actually transferring the data. In one embodiment, instead of the generating medical facility sending a full pre-anonymized resolution (e.g., 4K resolution) medical image to the server platform, the system instead involves a reduced resolution (even as low as 100×100 resolution) image, such as a thumbnail image, to the server platform. Because the areas of a medical image with text and those with important content are often quite distinct, the system is still able to identify areas to which to add deanonymization black boxes on the reduced resolution image. Information regarding the position of those black boxes within the image is then able to be transmitted back to the medical facility and a coordinate transform is able to be used to extrapolate where the corresponding black boxes should be added on the full resolution image. In this way, anonymization is able to occur without the medical facility itself having the software to perform the anonymization, but also without sending the pre-anonymized full resolution image outside of the medical facility. However, this method provides a distinct advantage even if performed entirely at the medical facility (i.e., without sending to an external server platform) relative to other in-house anonymization techniques, as it allows the anonymization to occur much more quickly.

The PHI detection system is operable to utilize a plurality of learning techniques including, but not limited to, machine learning (ML), artificial intelligence (AI), deep learning (DL), neural networks (NNs), artificial neural networks (ANNs), support vector machines (SVMs), Markov decision process (MDP), and/or natural language processing (NLP). The PHI detection system is operable to use any of the aforementioned learning techniques alone or in combination.

Further, the PHI detection system is operable to utilize predictive analytics techniques including, but not limited to, machine learning (ML), artificial intelligence (AI), neural networks (NNs) (e.g., long short term memory (LSTM) neural networks, convolutional neural networks, etc.), deep learning, historical data, and/or data mining to make future predictions and/or models. The PHI detection system is preferably operable to recommend and/or perform actions based on historical data, external data sources, ML, AI, NNs, and/or other learning techniques. The PHI detection system is operable to utilize predictive modeling and/or optimization algorithms including, but not limited to, heuristic algorithms, particle swarm optimization, genetic algorithms, technical analysis descriptors, combinatorial algorithms, quantum optimization algorithms, iterative methods, deep learning techniques, and/or feature selection techniques.

Figure 4:
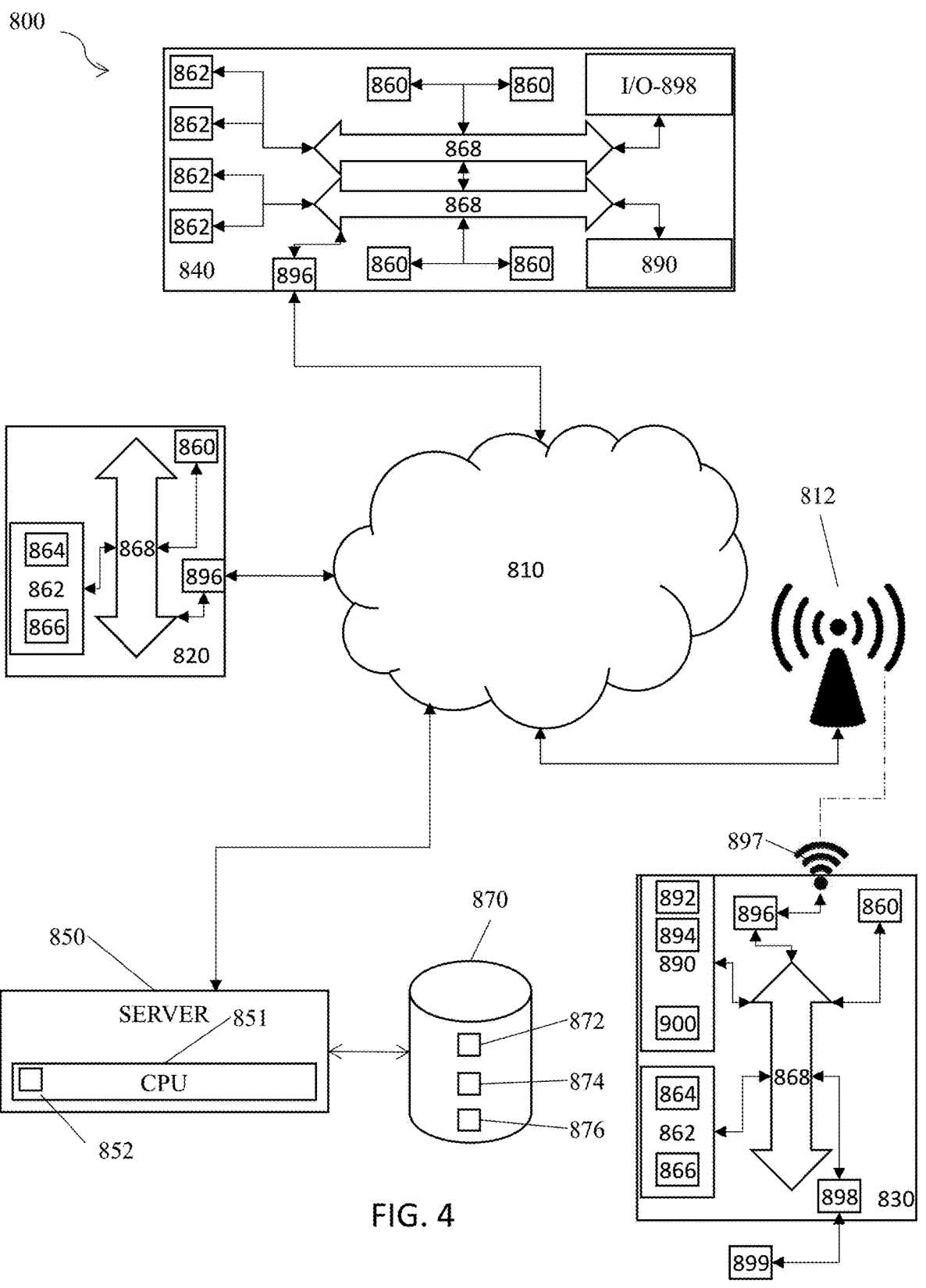
FIG. 4 is a schematic diagram of a system of the present invention.

FIG. 4 is a schematic diagram of an embodiment of the invention illustrating a computer system, generally described as 800, having a network 810, a plurality of computing devices 820, 830, 840, a server 850, and a database 870.

The server 850 is constructed, configured, and coupled to enable communication over a network 810 with a plurality of computing devices 820, 830, 840. The server 850 includes a processing unit 851 with an operating system 852. The operating system 852 enables the server 850 to communicate through network 810 with the remote, distributed user devices. Database 870 is operable to house an operating system 872, memory 874, and programs 876.

In one embodiment of the invention, the system 800 includes a network 810 for distributed communication via a wireless communication antenna 812 and processing by at least one mobile communication computing device 830. Alternatively, wireless and wired communication and connectivity between devices and components described herein include wireless network communication such as WI-FI, WORLDWIDE INTEROPERABILITY FOR MICROWAVE ACCESS (WIMAX), Radio Frequency (RF) communication including RF identification (RFID), NEAR FIELD COMMUNICATION (NFC), BLUETOOTH including BLUETOOTH LOW ENERGY (BLE), ZIGBEE, Infrared (IR) communication, cellular communication, satellite communication, Universal Serial Bus (USB), Ethernet communications, communication via fiber-optic cables, coaxial cables, twisted pair cables, and/or any other type of wireless or wired communication. In another embodiment of the invention, the system 800 is a virtualized computing system capable of executing any or all aspects of software and/or application components presented herein on the computing devices 820, 830, 840. In certain aspects, the computer system 800 is operable to be implemented using hardware or a combination of software and hardware, either in a dedicated computing device, or integrated into another entity, or distributed across multiple entities or computing devices.

By way of example, and not limitation, the computing devices 820, 830, 840 are intended to represent various forms of electronic devices including at least a processor and a memory, such as a server, blade server, mainframe, mobile phone, personal digital assistant (PDA), smartphone, desktop computer, netbook computer, tablet computer, workstation, laptop, and other similar computing devices. The components shown here, their connections and relationships, and their functions, are meant to be exemplary only, and are not meant to limit implementations of the invention described and/or claimed in the present application.

In one embodiment, the computing device 820 includes components such as a processor 860, a system memory 862 having a random access memory (RAM) 864 and a read-only memory (ROM) 866, and a system bus 868 that couples the memory 862 to the processor 860. In another embodiment, the computing device 830 is operable to additionally include components such as a storage device 890 for storing the operating system 892 and one or more application programs 894, a network interface unit 896, and/or an input/output controller 898. Each of the components is operable to be coupled to each other through at least one bus 868. The input/output controller 898 is operable to receive and process input from, or provide output to, a number of other devices 899, including, but not limited to, alphanumeric input devices, mice, electronic styluses, display units, touch screens, gaming controllers, joy sticks, touch pads, signal generation devices (e.g., speakers), augmented reality/virtual reality (AR/VR) devices (e.g., AR/VR headsets), or printers.

By way of example, and not limitation, the processor 860 is operable to be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that can perform calculations, process instructions for execution, and/or other manipulations of information.

In another implementation, shown as 840 in FIG. 4, multiple processors 860 and/or multiple buses 868 are operable to be used, as appropriate, along with multiple memories 862 of multiple types (e.g., a combination of a DSP and a microprocessor, a plurality of microprocessors, one or more microprocessors in conjunction with a DSP core).

Also, multiple computing devices are operable to be connected, with each device providing portions of the necessary operations (e.g., a server bank, a group of blade servers, or a multi-processor system). Alternatively, some steps or methods are operable to be performed by circuitry that is specific to a given function.

According to various embodiments, the computer system 800 is operable to operate in a networked environment using logical connections to local and/or remote computing devices 820, 830, 840 through a network 810. A computing device 830 is operable to connect to a network 810 through a network interface unit 896 connected to a bus 868. Computing devices are operable to communicate communication media through wired networks, direct-wired connections or wirelessly, such as acoustic, RF, or infrared, through an antenna 897 in communication with the network antenna 812 and the network interface unit 896, which are operable to include digital signal processing circuitry when necessary. The network interface unit 896 is operable to provide for communications under various modes or protocols.

In one or more exemplary aspects, the instructions are operable to be implemented in hardware, software, firmware, or any combinations thereof. A computer readable medium is operable to provide volatile or non-volatile storage for one or more sets of instructions, such as operating systems, data structures, program modules, applications, or other data embodying any one or more of the methodologies or functions described herein. The computer readable medium is operable to include the memory 862, the processor 860, and/or the storage media 890 and is operable be a single medium or multiple media (e.g., a centralized or distributed computer system) that store the one or more sets of instructions 900. Non-transitory computer readable media includes all computer readable media, with the sole exception being a transitory, propagating signal per se. The instructions 900 are further operable to be transmitted or received over the network 810 via the network interface unit 896 as communication media, which is operable to include a modulated data signal such as a carrier wave or other transport mechanism and includes any delivery media. The term "modulated data signal" means a signal that has one or more of its characteristics changed or set in a manner as to encode information in the signal.

Storage devices 890 and memory 862 include, but are not limited to, volatile and non-volatile media such as cache, RAM, ROM, EPROM, EEPROM, FLASH memory, or other solid state memory technology; discs (e.g., digital versatile discs (DVD), HD-DVD, BLU-RAY, compact disc (CD), or CD-ROM) or other optical storage; magnetic cassettes, magnetic tape, magnetic disk storage, floppy disks, or other magnetic storage devices; or any other medium that can be used to store the computer readable instructions and which can be accessed by the computer system 800.

In one embodiment, the computer system 800 is within a cloud-based network. In one embodiment, the server 850 is a designated physical server for distributed computing devices 820, 830, and 840. In one embodiment, the server 850 is a cloud-based server platform. In one embodiment, the cloud-based server platform hosts serverless functions for distributed computing devices 820, 830, and 840.

In another embodiment, the computer system 800 is within an edge computing network. The server 850 is an edge server, and the database 870 is an edge database. The edge server 850 and the edge database 870 are part of an edge computing platform. In one embodiment, the edge server 850 and the edge database 870 are designated to distributed computing devices 820, 830, and 840. In one embodiment, the edge server 850 and the edge database 870 are not designated for distributed computing devices 820, 830, and 840. The distributed computing devices 820, 830, and 840 connect to an edge server in the edge computing network based on proximity, availability, latency, bandwidth, and/or other factors.

It is also contemplated that the computer system 800 is operable to not include all of the components shown in FIG. 4, is operable to include other components that are not explicitly shown in FIG. 4, or is operable to utilize an architecture completely different than that shown in FIG. 4. The various illustrative logical blocks, modules, elements, circuits, and algorithms described in connection with the embodiments disclosed herein are operable to be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application (e.g., arranged in a different order or partitioned in a different way), but such implementation decisions should not be interpreted as causing a departure from the scope of the present invention.

Certain modifications and improvements will occur to those skilled in the art upon a reading of the foregoing description. The above-mentioned examples are provided to serve the purpose of clarifying the aspects of the invention and it will be apparent to one skilled in the art that they do not serve to limit the scope of the invention. All modifications and improvements have been deleted herein for the sake of conciseness and readability but are properly within the scope of the present invention.

The invention claimed is:

1. A system for reversibly deidentifying medical images, comprising:
   a server, including a processor and a memory, configured to receive medical images including one or more protected health information (PHI) regions;
   an artificial intelligence module configured to identify the one or more PHI regions in the medical images and define one or more bounding boxes around the identified one or more PHI regions;
   wherein the one or more bounding boxes are automatically clipped out of the medical images and one or more encrypted image files of the one or more bounding boxes are generated;
   wherein the locations and pixel values for pixels within the one or more bounding boxes are encrypted and where at least one cryptographic subkey is generated corresponding to the one or more bounding boxes; and
   wherein the at least one cryptographic subkey is operable to be used to readd the one or more encrypted image files into the medical images.

2. The system of claim 1, wherein the medical images are stored as Digital Imaging and Communication in Medicine (DICOM) files.

3. The system of claim 1, wherein separate cryptographic hashes are generated for a plurality of bounding boxes identified in a single one of the medical images.

4. The system of claim 1, wherein the at least one cryptographic subkey includes at least one public key and at least one private key.

5. The system of claim 1, wherein the encrypted locations and pixel values for pixels within the one or more bounding boxes are inserted into a header of a file for the medical images.

6. The system of claim 1, wherein the server automatically strips identifying metadata from each of the medical images.

7. The system of claim 1, wherein the artificial intelligence module includes an optical character recognition (OCR) tool.

8. The system of claim 1, wherein at least one master key is generated, wherein the master key is operable to readd all associated encrypted images files into one of the medical images.

9. A method for reversibly deidentifying medical images, comprising:
   receiving medical images including one or more protected health information (PHI) regions;
   an artificial intelligence module identifying the one or more PHI regions in the medical images and defining one or more bounding boxes around the identified one or more PHI regions;
   automatically clipping the one or more bounding boxes out of the medical images and generating one or more encrypted image files of the one or more bounding boxes;

encrypting the one or more bounding boxes based on locations and pixel values for pixels within the one or more bounding boxes;
   generating a cryptographic master key operable to be used to readd all associated encrypted image files back into one of the medical images; and
   based on the cryptographic master key, generating at least one cryptographic subkey operable to be used to readd one or more specific encrypted image files into the medical images.

10. The method of claim 9, further comprising saving the medical images as Digital Imaging and Communication in Medicine (DICOM) files.

11. The method of claim 9, wherein separate cryptographic subkeys are generated for a plurality of bounding boxes identified in a single one of the medical images.

12. The method of claim 9, wherein the at least one cryptographic hash includes at least one public key and at least one private key.

13. The method of claim 9, further comprising automatically inserting the one or more encrypted bounding boxes into a header of a file for the medical images.

14. The method of claim 9, further comprising automatically stripping identifying metadata from each of the medical images.

15. The method of claim 9, wherein the artificial intelligence module includes an optical character recognition (OCR) tool.

16. The method of claim 9, wherein the medical images are associated with metadata files, each including a plurality of fields, wherein the metadata files are encrypted, wherein at least one metadata key is generated, and wherein the at least one metadata key is operable to be used to decrypt one or more of the plurality of fields of the metadata files.

17. A system for deanonymization of medical images, comprising:
   a server, including a processor and a memory, configured to transmit medical image files to a recipient device;
   wherein the medical image files include a primary anonymized medical image, wherein the primary anonymized medical image includes one or more bounding boxes corresponding to removed protected health information (PHI), and one or more encrypted subimages of cropped portions of the primary anonymized medical images corresponding to the one or more bounding boxes;
   wherein the server receives a request from the recipient device designating at least one of the one or more bounding boxes to be removed or altered;
   wherein the server transmits at least one cryptographic key to the recipient device in response to the request; and
   wherein the at least one cryptographic key enables at least one of the one or more encrypted subimages to be reintegrated into the primary anonymized medical image.

18. The system of claim 17, wherein the medical image files are Digital Imaging and Communication in Medicine (DICOM) files.

19. The system of claim 17, wherein the at least one cryptographic key includes at least one private key.

20. The system of claim 17, wherein the request is automatically reviewed at least one artificial intelligence module to determine if the designated at least one of the one or more bounding boxes is likely to correspond to PHI.

* * * * *